United States Patent
Touati et al.

(10) Patent No.: US 11,166,887 B2
(45) Date of Patent: Nov. 9, 2021

(54) WATER-IN-OIL EMULSION COSMETIC

(71) Applicant: SHISEIDO COMPANY, LTD., Tokyo (JP)

(72) Inventors: Marianne Ayaka Touati, Yokohama (JP); Satoshi Yamaki, Yokohama (JP); Yurika Watanabe, Yokohama (JP); Takahiro Katori, Yokohama (JP); Yuko Nagare, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/620,234

(22) PCT Filed: Jun. 6, 2018

(86) PCT No.: PCT/JP2018/021657
§ 371 (c)(1),
(2) Date: Dec. 6, 2019

(87) PCT Pub. No.: WO2018/225765
PCT Pub. Date: Dec. 13, 2018

(65) Prior Publication Data
US 2020/0163847 A1 May 28, 2020

(30) Foreign Application Priority Data

Jun. 8, 2017 (JP) ............... JP2017-113235

(51) Int. Cl.
| | | |
|---|---|---|
| A61K 8/06 | (2006.01) | |
| A61K 8/25 | (2006.01) | |
| A61K 8/37 | (2006.01) | |
| A61K 8/81 | (2006.01) | |
| A61K 8/89 | (2006.01) | |
| A61Q 17/04 | (2006.01) | |

(52) U.S. Cl.
CPC ............ *A61K 8/064* (2013.01); *A61K 8/25* (2013.01); *A61K 8/37* (2013.01); *A61K 8/8152* (2013.01); *A61K 8/89* (2013.01); *A61Q 17/04* (2013.01)

(58) Field of Classification Search
CPC ...... A61K 8/064; A61K 8/19; A61K 2800/61; A61K 8/92; A61K 8/37
See application file for complete search history.

(56) References Cited

U.S. PATENT DOCUMENTS

| | | | | |
|---|---|---|---|---|
| 9,364,400 B2* | 6/2016 | Ikebe | ............... | A61K 8/894 |
| 10,426,714 B2* | 10/2019 | Yamaki | ............... | A61K 8/585 |
| 2012/0134939 A1* | 5/2012 | Ueda | ............... | A61K 8/73 |
| | | | | 424/59 |
| 2012/0251605 A1* | 10/2012 | Iimura | ............... | A61K 8/895 |
| | | | | 424/401 |
| 2013/0344013 A1* | 12/2013 | Ikebe | ............... | A61K 8/0254 |
| | | | | 424/59 |
| 2016/0096946 A1* | 4/2016 | Mutsuda | ............... | A61Q 17/04 |
| | | | | 424/59 |

FOREIGN PATENT DOCUMENTS

| | | |
|---|---|---|
| JP | 10-175819 | 6/1998 |
| JP | 2001-58934 | 3/2001 |
| JP | 2011-126832 | 6/2011 |
| JP | 2013-63954 | 4/2013 |
| WO | WO2016/068298 | 5/2016 |
| WO | WO 2017/057675 | 4/2017 |
| WO | WO-2017061604 A1 * | 4/2017 ............... A61K 8/41 |

OTHER PUBLICATIONS

PCT/JP2018/021657 International Search Report (ISR) and Written Opinion (WO), dated Jul. 10, 2018, 2 pages—English, 8 pages—Japanese.
PCT/JP2018/021657, Third Party Observation, mailed Sep. 30, 2019, 4 pages—English.

* cited by examiner

*Primary Examiner* — Mark V Stevens
(74) *Attorney, Agent, or Firm* — Andrew F. Young, Esq.; Nolte Lackenbach Siegel

(57) ABSTRACT

A water-in-oil emulsified cosmetic preparation that, even without substantially comprising a UV scattering agent: exhibits a higher UV protection effect than immediately after application, as a result of coming in contact with moisture, has excellent appearance, usability, and washability. The water-in-oil emulsified cosmetic preparation includes 6%-40% by mass of a UV absorber (A), an oil phase thickener (B), and at least one hydrophobic powder (C) selected from (i)-(iii), namely (i) hydrophobized talc, (ii) silicone powder having an average particle diameter of at least 30 μm, and (iii) crosslinked polymethyl methacrylate powder having a crosslinking density of at least 40%; and not including a UV scattering agent or containing no more than 6% by mass of same.

4 Claims, No Drawings

WATER-IN-OIL EMULSION COSMETIC

CROSS REFERENCE TO RELATED APPLICATIONS

This application relates to and claims priority as a § 371 national phase, from PCT/JP2018/021657 filed Jun. 6, 2018, the entire contents of which are incorporated herein by reference, which in turn claims priority from JP Ser. No.: 2017-113235 filed Jun. 8, 2017.

FIGURE SELECTED FOR PUBLICATION

None

TECHNICAL FIELD

The present invention relates to a water-in-oil emulsion cosmetic. More specifically, the present invention relates to a water-in-oil emulsion cosmetic that, by coming into contact with moisture such as perspiration, pool water, seawater or rain, provides ultraviolet-protection (blocking) effects that are higher than immediately after application even without blending a practical amount of an ultraviolet scattering agent and also has excellent properties in terms of the appearance after application, texture, and washability.

BACKGROUND ART

Protecting the skin and hair from damage due to ultraviolet (rays) is one of the important objectives for skin care, body care and hair care, and recently, it has come to be considered important to protect against ultraviolet rays, not only under harsh ultraviolet radiation conditions during outdoor activities such as bathing at the pool or at the beach in summer and skiing in winter, but also in everyday life. For this reason, cosmetics having ultraviolet protection (blocking) effects are desired even for use as normal (daily) makeup cosmetics, hair-care cosmetics or the like.

However, when a sunscreen cosmetic that is applied to skin comes into contact with moisture such as water or perspiration, an ultraviolet absorbing agent or an ultraviolet scattering agent drops off from the applied cosmetic, so that the ultraviolet protection effect unavoidably decreases. Therefore, various attempts have been made to improve the water resistance or the film strength of sunscreen cosmetics in order to prevent ultraviolet protection effects from weakening.

Among such attempts, in recent years, sunscreen cosmetics that have the unique effect wherein contact with moisture does not reduce the ultraviolet protection effects, but conversely improves the effects (hereinafter sometimes referred to as "ultraviolet protection performance improvement effects") have been proposed.

For example, Patent Document 1 describes that by blending an organically modified clay mineral, such as dimethyl distearyl ammonium hectorite, with an oil phase thickener such as a dextrin fatty acid ester, a sucrose fatty acid ester, and a fatty acid or a salt thereof, so as to have a formulated mass ratio relative to non-volatile liquid oils other than silicone oils, the ultraviolet protection effects, when coming into contact with moisture are improved compared to those immediately after application.

However, among sunscreen cosmetics that provide ultraviolet protection performance improvement effects, particularly those in water-in-oil emulsion form, it was normally preferable to blend 10 to 30% by mass, and at least about 6% by mass of an ultraviolet scattering agent into the cosmetic in order to achieve the effects, but when a large amount of the ultraviolet scattering agent is blended, the ultraviolet scattering agent, represented by titanium oxide (dioxide) and zinc oxide, scatters visible light in addition to ultraviolet rays. Thus, when the cosmetic is applied to skin, so-called "unnatural whiteness" occurs, and the appearance is made worse. Furthermore, the astringent effect of zinc oxide or the like imparts a feeling of dryness to the skin and may cause the feeling in use to become worse. Additionally, when an ultraviolet scattering agent having a hydrophobically treated surface is used in order to improve the dispersion stability or the like, it becomes difficult for the ultraviolet scattering agent to be washed away with soap or the like, so there is also a problem in that the washability is reduced and the like.

RELATED ART

Patent Documents

Patent Document 1: WO 2016/068298 A1

SUMMARY OF THE INVENTION

Problem to be Solved by the Invention

A purpose of the present invention is to provide a water-in-oil emulsion cosmetic that can achieve ultraviolet protection performance improvement effects even without blending in a practical amount of an ultraviolet scattering agent.

Means for Solving the Problem

The present inventors performed diligent studies towards solving the aforementioned problem, and as a result, discovered that, by using an ultraviolet ray absorbing agent in combination with an oil phase thickener and a specific hydrophobic powder, it is possible to obtain a water-in-oil emulsion cosmetic having ultraviolet protection effects while reducing the blended amount of or not blending an ultraviolet scattering agent and accordingly, the present invention is complete.

In other words, the present invention provides a water-in-oil emulsion cosmetic comprising:
(A) 6 to 40% by mass of an ultraviolet absorbing agent;
(B) an oil phase thickener; and
(C) at least one hydrophobic powder selected from a group consisting of (i) to (iii) below:
(i) a hydrophobically treated talc,
(ii) a silicone powder having an average particle size of 30 μm or larger, and
(iii) a crosslinked poly(methyl methacrylate) powder having a crosslink density of 40% or more;
wherein an ultraviolet scattering agent is not included or is included not more than 6% by mass.

Effects of the Invention

Due to the above-mentioned features, in the present invention, the ultraviolet protection effects after coming into contact with moisture such as perspiration, pool water, seawater or rain, are markedly-improved compared to that immediately after applying the cosmetic to the skin. Furthermore, the water-in-oil emulsion cosmetic of the present invention achieves excellent ultraviolet protection performance improvement effects even without blending in a practical amount of an ultraviolet scattering agent. Thus, unnatural whiteness does not tend to occur, powderiness and dryness can be suppressed, and the cosmetic can be easily removed with a normal cleanser or soap.

In other words, the present invention can provide a cosmetic having excellent properties in terms of the appearance after application, texture, and washability in addition to the ultraviolet protection performance improvement effects.

MODES FOR CARRYING OUT THE INVENTION

As mentioned above, the water-in-oil emulsion cosmetic of the present invention is characterized by containing (A) an ultraviolet absorbing agent, (B) an oil phase thickener, and (C) a hydrophobic powder. The respective components constituting the cosmetic of the present invention will be explained in detail below.

<(A) Ultraviolet Absorbing Agent>

As the (A) ultraviolet absorbing agent (hereinafter sometimes referred to simply as "component (A)") blended in the water-in-oil emulsion cosmetic according to the present invention can be a component that is normally blended into sunscreen cosmetics.

The ultraviolet absorbing agent used in the present invention is not particularly limited, but specific examples include organic ultraviolet absorbing agents such as ethylhexyl methoxycinnamate, octocrylene, dimethicodiethylbenzalmalonate, polysilicone-15, t-butyl methoxydibenzoylmethane, ethylhexyl triazone, diethylamino hydroxybenzoyl hexyl benzoate, bis-ethylhexyloxyphenol methoxyphenyl triazine, oxybenzone-3, methylene bis-benzotriazolyl tetramethylbutylphenol, phenylbenzimidazole sulfonic acid, homosalate and ethylhexyl salicylate.

The blended amount of component (A) should be 6 to 40% by mass, more preferably 8 to 35% by mass, and even more preferably 10 to 30% by mass relative to the overall amount of the water-in-oil emulsion cosmetic. If the blended amount of component (A) is less than 6% by mass, sufficient ultraviolet protection effects cannot be obtained, and even if more than 40% by mass thereof is blended, an increase in the ultraviolet protection effects that is commensurate with the blended amount cannot be expected, and this is undesirable for making the stability worse. Component (A) may be a single kind of component to be used or may be a combination of two or more kinds of components.

<(B) Oil Phase Thickener> The (B) oil phase thickener (hereinafter sometimes referred to simply as "component (B)") blended in the water-in-oil emulsion cosmetic according to the present invention is a substance that can adjust the viscosity of the oil phase in the water-in-oil emulsion cosmetic. As component (B), dextrin fatty acid esters, sucrose fatty acid esters, fatty acids or salts thereof, hardened vegetable oils, solid or semi-solid vegetable oils, organically modified clay minerals, glyceryl fatty acid esters and amino acid-based gelling agents are preferred.

Dextrin fatty acid esters are esters of dextrin or reduced dextrin having a higher fatty acid, which may be used without any particular restrictions as long as generally used in cosmetics. As the dextrin or reduced dextrin, the average degree of sugar polymerization is 3 to 100 is preferably used therefor. Additionally, as the fatty acid moiety of the dextrin fatty acid ester, a saturated fatty acid having 8 to 22 carbon atoms is preferably used. Specific examples include dextrin palmitate, dextrin oleate, dextrin stearate, dextrin myristate, dextrin (palmitate/2-ethylhexanoate) and the like.

As the sucrose fatty acid ester, one in which (the alkyl chain of) the fatty acid is linear or branched, saturated or unsaturated chain having 12 to 22 carbon atoms, is preferably used. Specific examples include sucrose caprylic acid esters, sucrose capric acid esters, sucrose lauric acid esters, sucrose myristic acid esters, sucrose palmitic acid esters, sucrose stearic acid esters, sucrose oleic acid esters, sucrose erucic acid esters, sucrose acetate/stearate and the like.

The fatty acid may be solid at ambient temperature, and examples include myristic acid, palmitic acid, stearic acid, behenic acid and the like. Additionally, the fatty acid salt may be a calcium salt, a magnesium salt, an aluminum salt or the like of the above.

Examples of the hardened vegetable oil include hardened palm kernel oil, hardened castor oil, hydrogenated peanut oil, hydrogenated rapeseed oil, hydrogenated palm oil, hydrogenated camellia oil, hydrogenated soybean oil, hydrogenated olive oil, hydrogenated macadamia nut oil, hydrogenated sunflower oil, hydrogenated wheat germ oil, hydrogenated rice germ oil, hydrogenated rice bran oil, hydrogenated cottonseed oil, hydrogenated avocado oil and the like.

Additionally, as well as the hardened vegetable oils, a vegetable oil that is solid or semi-solid at room temperature can be used. In such a case, a solid oil refers to an oil that is solid at 25° C., and a semi-solid oil is in between solid and liquid oil at 25° C. More specifically, such a semi-solid oil has preferably a melting point between 44° C. and 90° C., the viscosity thereof measured by a B-type viscometer at 25° C. is 5000 mPa·s or higher, or furthermore, 10,000 mPa·s or higher, is preferable. Examples of vegetable oils that are solid or semi-solid at room temperature include cacao butter, coconut oil, palm oil, palm kernel oil, Japan tallow, rhea butter and the like.

As the organically modified clay mineral, it is possible to use a clay mineral modified by a quaternary ammonium salt type cationic surfactant, represented by the following general formula (1), which is a colloidal hydrated aluminum silicate having a three-layered structure.

$$(X,Y)_{2-3}(Si,Al)_4O_{10}(OH)_2Z_{1/3} \cdot nH_2O \tag{1}$$

where X=Al, Fe(III), Mn(III) or Cr(III); Y=Mg, Fe(II), Ni, Zn or Li; and Z=K, Na or Ca.

Specifically, such an organically modified clay mineral can be obtained by treating a natural or synthetic montmorillonite (wherein an (OH) group of the synthetic montmorillonite is substituted with fluorine) (e.g., such as Veegum®, Kunipia, Laponite® are commercially available), and related including such as saponite and hectorite, or a synthetic mica known under the name of sodium silicic mica or sodium or lithium taeniolite (e.g., such as Dimonite, Topy Industries, Ltd., is commercially available) with a quaternary ammonium salt type cationic surfactant.

The quaternary ammonium salt type cationic surfactant used in this case is represented by the following general (chemical) formula (2):

[Chemical Formula 1]

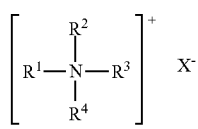

(2)

where $R^1$ represents a benzyl group or an alkyl group having 10 to 22 carbon atoms, $R^2$ represents an alkyl group having 10 to 22 carbon atoms or a methyl group, $R^3$ and $R^4$ represent alkyl groups or hydroxyalkyl groups having 1 to 3 carbon atoms, and X represents a halogen atom or a methylsulfate residue.

Examples of the quaternary ammonium salt type cationic surfactant include dodecyltrimethylammonium chloride, myristyltrimethylammonium chloride, cetyltrimethylammonium chloride, stearyltrimethylammonium chloride, arachyltrimethylammonium chloride, behenyltrimethylammonium chloride, myristyldimethylethylammonium chloride, cetyldimethylethylammonium chloride, stearyldimethylethylammonium chloride, arachyldimethylethylammonium chloride, behenyldimethylethylammonium chloride, myristyldiethylmethylammonium chloride, cetyldiethylmethylammonium chloride, stearyldiethylmethylammonium chloride, arachyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcetylammonium chloride, benzylmethylethylstearylammonium chloride, dibehenyldihydroxyethylammonium chloride, and corresponding bromides and the like, and further thereto, dipalmitylpropylethylammonium methylsulfate and the like. When carrying out the present invention, one or more of these compounds may be arbitrarily selected.

Representative examples of organically modified clay minerals include dimethyl distearyl ammonium hectorite (distearyldimonium hectorite), dimethylalkylammonium hectorite, benzyldimethylstearylammonium hectorite, distearyldimethylammonium chloride-treated aluminum-magnesium silicate and the like. Of these, dimethyl distearyl ammonium hectorite is particularly preferred. As commercial products, Bentone 27 (benzyldimethylstearylammonium chloride-treated hectorite, manufactured by Elementis Japan KK) and Bentone 38 (distearyldimethylammonium chloride-treated hectorite, manufactured by Elementis Japan KK) are preferred.

Glyceryl fatty acid esters are esterification reaction products obtained by reacting glycerin, a diprotic acid having 18 to 28 carbon atoms, and a fatty acid having 8 to 28 carbon atoms (excluding diprotic acids) and may be used without any particular restrictions as long as they are generally used in cosmetics. Specific examples include glyceryl (behenate/isostearate/eicosanedioate), glyceryl (behenate/eicosanedioate) and polyglyceryl-10 (behenate/eicosanedioate), etc.

Examples of amino acid-based gelling agents include dibutyl lauroyl glutamide, dibutyl ethylhexanoyl glutamide, polyamide-8, polyamide-3, N-lauroyl-L-glutamic acid dibutyl amide and the like.

Component (B) may be used as a single component or may be a combination of two or more kinds (of components). The blended amount of component (B) is preferably 0.1 to 15% by mass, more preferably 0.2 to 10% by mass, and even more preferably 0.4 to 8% by mass relative to the overall mass of the water-in-oil emulsion cosmetic. If the blended amount of component (B) is less than 0.1% by mass, there is a tendency for the ultraviolet blocking effects to become worse upon coming into contact with moisture, and if more than 15% by mass is blended in, the viscosity becomes high and undesirable in terms of texture, such as becoming difficult to spread over the skin.

<(C) Hydrophobic Powder>

The hydrophobic powder (hereinafter referred to simply as "component (C)" in some cases) blended into the water-in-oil emulsion cosmetic according to the present invention comprises powder particles that interact a little with water and have low affinity to water. Such hydrophobic powders are normally blended into cosmetics for the purpose of improving the texture. Hydrophobic powders include powders obtained by hydrophobically treating either hydrophilic or hydrophobic powder particles as base materials as well as powder particles of materials that are essentially hydrophobic.

The (C) hydrophobic powder blended into the water-in-oil emulsion cosmetic according to the present invention is preferably selected from a group consisting of the following components (i) to (iii):
(i) a hydrophobically treated talc;
(ii) a silicone powder having an average particle size of 30 μm or larger; and
(iii) a crosslinked poly(methyl methacrylate) powder having a crosslink density of 40% or higher.

(i) Hydrophobically treated talc

Hydrophobically treated talc is a powder having talc, which is a silicic acid salt-based clay mineral, as a base material, the surface of which is hydrophobically treated. As indicated in the examples described below, hydrophobically treated talc is able to provide ultraviolet protection performance improvement effects regardless of the type of hydrophobic treatment, so that such a talc is particularly preferable as the component (C).

The hydrophobic treatment is not particularly restricted, but may, for example, be a silicone treatment (treatment with a silicone oil such as methylhydrogen polysiloxane, dimethyl polysiloxane or methylphenyl polysiloxane; an alkylsilane such as methyltrimethoxysilane, ethyltrimethoxysilane, hexyltrimethoxysilane or octyltrimethoxysilane; or a fluoroalkylsilane such as trifluoromethylethyl trimethoxysilane or heptadecafluorodecyl trimethoxysilane), a fatty acid treatment (treatment with palmitic acid, isostearic acid, stearic acid, lauric acid, myristic acid, behenic acid, oleic acid, rosin acid, 12-hydroxystearic acid or the like), a fatty acid soap treatment (treatment with aluminum stearate, calcium stearate, 12-hydroxystearic acid or the like), or a fatty acid ester treatment (treatment with a dextrin fatty acid ester, a cholesterol fatty acid ester, a sucrose fatty acid ester, a starch fatty acid ester or the like). These hydrophobic treatments may be performed in accordance with conventional methods. With regard to hydrophobic treatments, silicone treatments are suitable for being able to impart such as high stability to the powder particles.

As a hydrophobically treated talc, a commercial product can be used and an example thereof is "calcium stearate-treated talc" (Fujimoto Chemicals Co., Ltd.).

(ii) Silicone powder having average particle size of 30 pin or larger

As the silicone powder, one that is normally used as a cosmetic raw material may be used, as long as the average particle size is 30 μm or larger. As examples of silicone powders, methylpolysiloxane network polymers, crosslinked methylpolysiloxane, crosslinked silicone-network silicone block copolymers, silylated silica and the like are known. Of these, crosslinked silicone-network silicone block copolymers are particularly preferred.

The average particle size of the silicone powder is 30 μm or larger, more preferably 32 μm or larger, and even more preferably 35 μm or larger. If the average particle size is smaller than 30 μm, then there is a tendency for the ultraviolet protection effects to become worse upon coming into contact with moisture. On the other hand, although the upper limit of the average particle size is not particularly restricted, it should preferably be 70 μm or smaller in view of the texture and the stability. The particle size distribution of the silicone powder should preferably be from 5 to 100 μm. The average particle size of the silicone powder can be measured by a laser diffraction/scattering method.

An example of a silicone powder commercial product that can be used is "KSP-102" (manufactured by Shin-etsu Chemical Co., Ltd. (vinyl dimethicone/methicone silsesquioxane) crosspolymer, average particle size 30 μm).

(iii) Crosslinked poly(methyl methacrylate) powder having crosslink density of 40% or higher As the crosslinked poly(methyl methacrylate) powder (PMMA powder), any type having a crosslink density of 40% or higher may be used. The crosslink density of the crosslinked poly(methyl methacrylate) powder is 40% or higher, more preferably 42% or higher, and even more preferably 45% or higher. When a PMMA powder in which the crosslink density is less than 40% is used, there is a tendency for the ultraviolet protection effect upon coming into contact with moisture to become worse. On the other hand, although the upper limit of the crosslink density is not particularly restricted, it should preferably be 60% or less in view of the texture. The crosslink density may be determined by various generally known methods such as a solvent swelling method.

The component (C) selected from a group consisting of components (i) to (iii) above may be a single kind thereof or may be a combination of two or more kinds. The blended amount of the component (C) should preferably be 3 to 30% by mass, more preferably 5 to 25% by mass, and even more preferably 5 to 20% by mass relative to the overall mass of the water-in-oil emulsion cosmetic. If the blended amount of component (B) is less than 3% by mass, then there is a tendency for the ultraviolet protection effects upon coming into contact with moisture to become worse, and if more than 30% by mass is blended, the texture may become worse with regard to such as squeakiness, smudges and stickiness occurring, and the cosmetic may become difficult to be formulated.

<Ultraviolet Scattering Agent>

The water-in-oil emulsion cosmetic of the present invention can achieve sufficient ultraviolet protection performance improvement effects by containing the above-mentioned components (A) to (C), even without blending in an ultraviolet scattering agent.

However, a small amount of an ultraviolet scattering agent can be blended for the purpose of further improving the protection effects against ultraviolet rays. When blending an ultraviolet scattering agent into the water-in-oil emulsion cosmetic of the present invention, an amount thereof is 6% by mass or less, preferably 5% by mass or less, more preferably 4% by mass or less, and particularly preferably 3% by mass or less relative to the overall amount of the water-in-oil emulsion cosmetic in order to suppress unnatural whiteness and texture-worsening due to the ultraviolet scattering agent.

The ultraviolet scattering agent that may be blended in the water-in-oil emulsion cosmetic of the present invention is not particularly limited, and an ultraviolet scattering agent that is normally used in cosmetics may be used. Examples of ultraviolet scattering agents include fine-particle metal oxides such as zinc oxide, titanium oxide, iron oxide, cerium oxide and tungsten oxide, and surfaces of such metal oxides have been subjected to various hydrophobic surface treatments. As the hydrophobic surface treatment agent that are generally used in the cosmetic field including, for example, silicones such as dimethicone and alkyl-modified silicone, alkoxysilanes such as octyltriethoxysilane, dextrin fatty acid esters such as dextrin palmitate, and fatty acids such as stearic acid may be used.

Aside from the above-mentioned essential components, the water-in-oil emulsion cosmetic of the present invention may appropriately contain, as needed, components that are normally used in cosmetics such as, for example, oils, water, alcohols, surfactants, oil-based active agents, water-based active agents, water phase thickeners, humectants and antioxidants.

Among the above, a surfactant that may be used in the present invention is preferably a surfactant having an HLB lower than 8, particularly a silicone-based surfactant, in order to attain a water-in-oil emulsion state.

Examples of silicone-based surfactants having an HLB lower than 8 include polyoxyalkylene-modified silicones, polyoxyalkylene/alkyl co-modified silicones, polyglycerin-modified silicones and/or polyglycerin/alkyl co-modified silicones. Specific examples include KF-6017 (PEG-10 dimethicone, manufactured by Shin-etsu Chemical Co., Ltd.), KF-6028 (PEG-9 polydimethylsiloxyethyl dimethicone, manufactured by Shin-etsu Chemical Co., Ltd.), ABIL EM 90 (cetyl PEG/PPG-10/1 dimethicone, manufactured by Evonik Goldschmidt Corp.) and KF-6038 (lauryl PEG-9 polydimethylsiloxyethyl dimethicone, manufactured by Shin-etsu Chemical Co., Ltd.), bis-butyl dimethicone polyglyceryl-3 and the like.

The blended amount of the silicone-based surfactant should preferably be 0.1 to 8% by mass, more preferably 0.2 to 7% by mass, even more preferably 0.4 to 5% by mass relative to the overall amount of the water-in-oil emulsion cosmetic.

The water-in-oil emulsion cosmetic of the present invention may be provided not only, for example, as a sunscreen cream, a sunscreen milky lotion or a sunscreen lotion, but may also be used as a foundation, a makeup base, a makeup cosmetic, a hair cosmetic or the like imparted with sunscreen effects, and may be produced by a conventional method.

EXAMPLES

The present invention will be explained in further detail by referring to specific examples below, but the present invention is not limited to the examples indicated below. Additionally, the blended amounts in the following examples and the like are in % by mass unless specially indicated otherwise.

Examples 1 to 10 and Comparative Examples 1 to 3

Water-in-oil emulsion cosmetics having the compositions indicated in Tables 1 and 2 below were prepared by heating and melting the oil-based components and dispersing the powder therein, adding the separately mixed water phase thereto, and emulsifying the mixture by stirring.

Method for Measuring Ultraviolet Protection Performance Improvement Effects

Cosmetics (samples) according to respective examples were dripped, in the amount of 2 mg/cm$^2$, onto measurement plates (S plates) (5×5 cm V-grooved PMMA plates, SPFMASTER-PA01), which were coated by finger for 60 seconds, and dried for 15 minutes. Thereafter, the absorbances of the formed coating films were measured by a U-3500 selfrecording spectrophotometer manufactured by Hitachi, Ltd. With an uncoated plate as the control, absorbances (Abs) were computed from the expression indicated below, and the measurement values at 280 nm to 400 nm were summed.

$$Abs=-\log(T/To)$$

T: transmittance of sample, To: transmittance of uncoated plate

The measured plates were well-immersed in water having a hardness of 50 to 500, then agitated while still immersed in water for 30 minutes (300 rpm with a three-one motor). Thereafter, the samples were dried for approximately 15 to 30 minutes until water droplets on the surfaces disappeared, and the absorbances were measured again. The Abs variation rate (the expression below) was computed, as the ultraviolet protection performance improvement effects, from the cumulative Abs values before and after immersion in water.

Ultraviolet protection performance improvement effects:

Abs variation rate (%)=(cumulative Abs value after water immersion)/(cumulative Abs value before water immersion)×100

TABLE 1

|  | Ex. 1 | Ex. 2 | Comp. Ex. 1 | Comp. Ex. 2 | Comp. Ex. 3 |
| --- | --- | --- | --- | --- | --- |
| Purified water | bal | bal | bal | bal | bal |
| 2-Ethylhexyl para-methoxycinnamate | 8 | 8 | 8 | 8 | 8 |
| Diethylamino hydroxybenzoyl hexyl benzoate | 2 | 2 | 2 | 2 | 2 |
| Dextrin palmitate | 3 | 3 | 3 | 3 | 3 |
| Cetyl 2-ethylhexanoate | 5 | 5 | 5 | 5 | 5 |
| Glyceryl tri-2-ethylhexanoate | 5 | 5 | 5 | 5 | 5 |
| Diisopropyl sebacate | 5 | 5 | 5 | 5 | 5 |
| Dimethyl polysiloxane (*1) | 2 | 2 | 2 | 2 | 2 |
| Decamethylcyclopentasiloxane | 30 | 30 | 30 | 30 | 30 |
| Lauryl PEG-9 polydimethylsiloxyethyl dimethicone | 3 | 3 | 3 | 3 | 3 |
| Decamethyltetrasiloxane | 10 | 10 | 10 | 10 | 10 |
| Dimethyl distearyl ammonium hectorite | 0.5 | 0.5 | 0.5 | 0.5 | 0.5 |
| Ethanol (*2) | 10 | 10 | 10 | 10 | 10 |
| Glycerin | 1 | 1 | 1 | 1 | 1 |
| Trisodium edetate | s.a. | s.a. | s.a. | s.a. | s.a. |
| Fragrance | s.a. | s.a. | s.a. | s.a. | s.a. |
| Table salt | s.a. | s.a. | s.a. | s.a. | s.a. |
| Calcium stearate-treated talc (average particle size 7 μm) | 10 | — | — | — | — |
| Crosslinked silicone-network silicone block copolymer (average particle size 30 μm) | — | 10 | — | — | — |
| Crosslinked silicone-network silicone block copolymer (average particle size 5 μm) | — | — | 10 | — | — |
| Methyl siloxane network polymer (average particle size 6 μm) | — | — | — | 10 | — |
| Silicic anhydride (average particle size 5 μm) | — | — | — | — | 10 |
| Abs variation rate (%) | 119.5 | 143.1 | 91.1 | 82.9 | 54.1 |

(*1) KF-96A-6T (Shin-etsu Chemical Co., Ltd.)

(*2) Synthetic alcohol 95% (Japan Alcohol Trading Co., Ltd.)

TABLE 2

|  | Ex. 3 | Ex. 4 | Ex. 5 | Ex. 6 | Ex. 7 | Ex. 8 | Ex. 9 | Ex. 10 |
| --- | --- | --- | --- | --- | --- | --- | --- | --- |
| Purified water | bal | bal | bal | bal | bal | bal | bal | bal |
| 2-Ethylhexyl para-methoxycinnamate | 8 | 8 | 8 | 8 | 8 | 8 | 8 | 8 |
| Diethylamino hydroxybenzoyl hexyl benzoate | 2 | 2 | 2 | 2 | 2 | 2 | 2 | 2 |
| Dextrin palmitate | 3 | 3 | 3 | 3 | 3 | 3 | 3 | 3 |
| Cetyl 2-ethylhexanoate | 5 | 5 | 5 | 5 | 5 | 5 | 5 | 5 |
| Glyceryl tri-2-ethylhexanoate | 5 | 5 | 5 | 5 | 5 | 5 | 5 | 5 |
| Diisopropyl sebacate | 5 | 5 | 5 | 5 | 5 | 5 | 5 | 5 |
| Dimethyl polysiloxane (*1) | 2 | 2 | 2 | 2 | 2 | 2 | 2 | 2 |
| Decamethylcyclopentasiloxane | 30 | 30 | 30 | 30 | 30 | 30 | 30 | 30 |
| Lauryl PEG-9 polydimethylsiloxyethyl dimethicone | 3 | 3 | 3 | 3 | 3 | 3 | 3 | 3 |
| Decamethyltetrasiloxane | 10 | 10 | 10 | 10 | 10 | 10 | 10 | 10 |
| Dimethyl distearyl ammonium hectorite | 0.5 | 0.5 | 0.5 | 0.5 | 0.5 | 0.5 | 0.5 | 0.5 |
| Ethanol (*2) | 10 | 10 | 10 | 10 | 10 | 10 | 10 | 10 |
| Glycerin | 1 | 1 | 1 | 1 | 1 | 1 1 | 1 | 1 |
| Trisodium edetate | s.a. | s.a. | s.a. | s.a. | s.a. | s.a. | s.a. | s.a. |
| Fragrance | s.a. | s.a. | s.a. | s.a. | s.a. | s.a. | s.a. | s.a. |
| Table salt | s.a. | s.a. | s.a. | s.a. | s.a. | s.a. | s.a. | s.a. |
| Calcium stearate-treated talc (average particle size 22 μm) | 10 | — | — | — | — | — | — | — |

TABLE 2-continued

|  | Ex. 3 | Ex. 4 | Ex. 5 | Ex. 6 | Ex. 7 | Ex. 8 | Ex. 9 | Ex. 10 |
|---|---|---|---|---|---|---|---|---|
| Calcium stearate-treated talc (average particle size 7 μm) | — | 10 | — | — | — | — | — | — |
| Calcium stearate-treated talc (average particle size 14 μm) | — | — | 10 | — | — | — | — | — |
| Dimethylpolysiloxane-treated talc (average particle size 12 μm) | — | — | — | 10 | — | — | — | — |
| Perfluorooctyltriethoxysilane/alkyl acrylate copolymer methyl polysiloxane ester-treated talc (average particle size 12 μm) | — | — | — | — | 10 | — | — | — |
| Carboxydecyl trisiloxane zinc salt-treated talc (average particle size 12 μm) | — | — | — | — | — | 10 | — | — |
| Triethoxysilylethyl polydimethylsiloxyethyl hexyl dimethicone-treated talc (average particle size 15 μm) | — | — | — | — | — | — | 10 | — |
| Triethoxysilylethyl polydimethylsiloxyethyl hexyl dimethicone-treated talc (average particle size 12 μm) | — | — | — | — | — | — | — | 10 |
| Abs variation rate (%) | 119.5 | 113.3 | 116.2 | 113.4 | 118.4 | 118.8 | 109.7 | 112.4 |

(*1) KF-96A-6T (Shin-etsu Chemical Co., Ltd.)
(*2) Synthetic alcohol 95% (Japan Alcohol Trading Co., Ltd.)

As shown in Table 1 and Table 2 above, it was confirmed that, even when absolutely no ultraviolet scattering agent was included, by blending hydrophobically treated talc (Examples 1 and 3 to 10) or a silicone powder having an average particle size of 30 μm or larger (Example 2), as a hydrophobic powder, in addition to an oil phase thickener, the Abs variation rate exceeded 100%, i.e., the ultraviolet protection effects after immersion in water were improved in comparison to those before immersion in water. In particular, it was confirmed that hydrophobically treated talc achieved ultraviolet protection performance improvement effects regardless of the type of hydrophobic treatment (Examples 3 to 10).

On the other hand, when a silicone powder or silicic anhydride (silica powder) having an average particle size smaller than 30 μm was used, the Abs variation rate became less than 100% and ultraviolet protection performance improvement effects were not observed (Comparative Examples 1 to 3).

Examples 11 to 19 and Comparative Examples 4 to 7

Water-in-oil emulsion cosmetics having the compositions listed in Table 3 below were prepared, and the Abs variation rates before and after water immersion were determined in the same manner as that described above.

TABLE 3A

|  | Comp. Ex. 4 | Comp. Ex. 5 | Comp. Ex. 6 | Comp. Ex. 7 | Ex. 11 | Ex. 12 | Ex. 13 |
|---|---|---|---|---|---|---|---|
| Octocrylene | 5 | 5 | 5 | 5 | 5 | 5 | 5 |
| 2-Ethylhexyl para-methoxycinnamate | 3 | 3 | 3 | 3 | 3 | 3 | 3 |
| 2,4-bis-[{4-(2-ethylhexyloxy)-2-hydroxy}-phenyl]-6-(4-methoxyphenyl)-1,3,5-triazine | 2 | 2 | 2 | 2 | 2 | 2 | 2 |
| Diethylamino hydroxybenzoyl hexyl benzoate | 2 | 2 | 2 | 2 | 2 | 2 | 2 |
| 4-tert-Butyl-4'-methoxydibenzoylmethane | 2.5 | 2.5 | 2.5 | 2.5 | 2.5 | 2.5 | 2.5 |
| Dextrin palmitate | 2 | 2 | 2 | 2 | 2 | 2 | 2 |
| Sucrose acetate stearate | 2 | 2 | 2 | 2 | 2 | 2 | 2 |
| Trimethylsiloxysilicic acid | 1.5 | 1.5 | 1.5 | 1.5 | 1.5 | 1.5 | 1.5 |
| Polyoxybutylene (9) polyoxypropylene (1) glycol | 2 | 2 | 2 | 2 | 2 | 2 | 2 |
| Isostearic acid | 0.5 | 0.5 | 0.5 | 0.5 | 0.5 | 0.5 | 0.5 |
| Diisopropyl sebacate | 10 | 10 | 10 | 10 | 10 | 10 | 10 |
| Isopropyl myristate | 5 | 5 | 5 | 5 | 5 | 5 | 5 |
| Glyceryl tri-2-ethylhexanoate | 5 | 5 | 5 | 5 | 5 | 5 | 5 |
| Methyl polysiloxane | 5 | 5 | 5 | 5 | 5 | 5 | 5 |
| Dimethyl distearyl ammonium hectorite | 0.5 | 0.5 | 0.5 | 0.5 | 0.5 | 0.5 | 0.5 |
| Decamethylcyclopentasiloxane | 12 | 12 | 12 | 12 | 12 | 12 | 12 |
| Lauryl PEG-9 polydimethylsiloxyethyl dimethicone | 3 | 3 | 3 | 3 | 3 | 3 | 3 |
| Purified water | bal | bal | bal | bal | bal | bal | bal |
| Table salt | s.a. | s.a. | s.a. | s.a. | s.a. | s.a. | s.a. |
| Trisodium edetate | s.a. | s.a. | s.a. | s.a. | s.a. | s.a. | s.a. |
| Fragrance | s.a. | s.a. | s.a. | s.a. | s.a. | s.a. | s.a. |
| Glycerin | 1 | 1 | 1 | 1 | 1 | 1 | 1 |
| Xylitol | 1 | 1 | 1 | 1 | 1 | 1 | 1 |

TABLE 3A-continued

|  | Comp. Ex. 4 | Comp. Ex. 5 | Comp. Ex. 6 | Comp. Ex. 7 | Ex. 11 | Ex. 12 | Ex. 13 |
|---|---|---|---|---|---|---|---|
| Alcohol | 6 | 6 | 6 | 6 | 6 | 6 | 6 |
| Hydrogendimethicone-treated pearling agent (mica/titanium oxide) | 3 | 3 | 3 | 3 | 3 | 3 | 3 |
| Methylhydrogenpolysiloxane-treated pearling agent (mica/titanium oxide/tin oxide) | 0.3 | 0.3 | 0.3 | 0.3 | 0.3 | 0.3 | 0.3 |
| Crosslinked poly(methyl methacrylate) (average particle size 8 μm) low crosslink density type (crosslink density 10%) | 15 | — | — | — | — | — | — |
| Calcium stearate-treated talc (average particle size 7 μm) | — | — | — | — | 15 | — | — |
| Silicic anhydride (average particle size 5 μm) | 1 | 16 | 1 | 1 | 1 | 1 | 1 |
| Crosslinked silicone-network silicone block copolymer (average particle size 5 μm) | — | — | 15 | — | — | — | — |
| Dimethylpolysiloxane-treated talc (average particle size 12 μm) | — | — | — | — | — | 15 | — |
| Methyl siloxane network polymer (average particle size 6 μm) | — | — | — | 15 | — | — | — |
| Crosslinked poly(methyl methacrylate) (average particle size 8 μm) high crosslink density type (crosslink density 50%) | — | — | — | — | — | — | 15 |
| Abs variation rate (%) | 98.2 | 49.5 | 96.5 | 92.1 | 112.4 | 105.3 | 105.4 |

TABLE 3B

|  | Ex. 14 | Ex. 15 | Ex. 16 | Ex. 17 | Ex. 18 | Ex. 19 |
|---|---|---|---|---|---|---|
| Octocrylene | 5 | 5 | 5 | 5 | 5 | 5 |
| 2-Ethylhexyl para-methoxycinnamate | 3 | 3 | 3 | 3 | 3 | 3 |
| 2,4-bis-[{4-(2-ethylhexyloxy)-2-hydroxy}-phenyl]-6-(4-methoxyphenyl)-1,3,5-triazine | 2 | 2 | 2 | 2 | 2 | 2 |
| Diethylamino hydroxybenzoyl hexyl benzoate | 2 | 2 | 2 | 2 | 2 | 2 |
| 4-tert-Butyl-4'-methoxydibenzoylmethane | 2.5 | 2.5 | 2.5 | 2.5 | 2.5 | 2.5 |
| Dextrin palmitate | 2 | 2 | 2 | 2 | 2 | 2 |
| Sucrose acetate stearate | 2 | 2 | 2 | 2 | 2 | 2 |
| Trimethylsiloxysilicic acid | 1.5 | 1.5 | 1.5 | 1.5 | 1.5 | 1.5 |
| Polyoxybutylene (9) polyoxypropylene (1) glycol | 2 | 2 | 2 | 2 | 2 | 2 |
| Isostearic acid | 0.5 | 0.5 | 0.5 | 0.5 | 0.5 | 0.5 |
| Diisopropyl sebacate | 10 | 10 | 10 | 10 | 10 | 10 |
| Isopropyl myristate | 5 | 5 | 5 | 5 | 5 | 5 |
| Glyceryl tri-2-ethylhexanoate | 5 | 5 | 5 | 5 | 5 | 5 |
| Methyl polysiloxane | 5 | 5 | 5 | 5 | 5 | 5 |
| Dimethyl distearyl ammonium hectorite | 0.5 | 0.5 | 0.5 | 0.5 | 0.5 | 0.5 |
| Decamethylcyclopentasiloxane | 12 | 12 | 12 | 12 | 12 | 12 |
| Lauryl PEG-9 polydimethylsiloxyethyl dimethicone | 3 | 3 | 3 | 3 | 3 | 3 |
| Purified water | bal | bal | bal | bal | bal | bal |
| Table salt | s.a. | s.a. | s.a. | s.a. | s.a. | s.a. |
| Trisodium edetate | s.a. | s.a. | s.a. | s.a. | s.a. | s.a. |
| Fragrance | s.a. | s.a. | s.a. | s.a. | s.a. | s.a. |
| Glycerin | 1 | 1 | 1 | 1 | 1 | 1 |
| Xylitol | 1 | 1 | 1 | 1 | 1 | 1 |
| Alcohol | 6 | 6 | 6 | 6 | 6 | 6 |
| Hydrogendimethicone-treated pearling agent (mica/titanium oxide) | 3 | 3 | 3 | 3 | — | — |
| Methylhydrogenpolysiloxane-treated pearling agent (mica/titanium oxide/tin oxide) | 0.3 | 0.3 | 0.3 | 0.3 | — | — |
| Crosslinked poly(methyl methacrylate) (average particle size 8 μm) low crosslink density type (crosslink density 10%) | 7 | 5 | 10 | 7 | 10 | 10 |
| Calcium stearate-treated talc (average particle size 7 μm) | 8 | 10 | 5 | 8 | 3 | 1 |
| Silicic anhydride (average particle size 5 μm) | 1 | 1 | 1 | 1 | — | — |
| Crosslinked silicone-network silicone block copolymer (average particle size 5 μm) | 0.5 | — | — | 0.5 | 1 | 1 |
| Dimethylpolysiloxane-treated talc (average particle size 12 μm) | — | — | — | — | — | — |
| Methyl polysiloxane network polymer (average particle size 6 μm) | — | — | — | — | — | — |
| Crosslinked poly(methyl methacrylate) (average particle size 8 μm) high crosslink density type (crosslink density 50%) | — | — | — | — | — | — |
| Abs variation rate (%) | 102.8 | 109.9 | 105.1 | 106.2 | 115.9 | 115.0 |

As shown in Table 3, it was confirmed that, by blending in, as a hydrophobic powder, hydrophobically treated talc (Examples 11, 12 and 14-19) or a crosslinked poly(methyl methacrylate) powder having a crosslink density of 40% or higher (Example 13), it is possible to achieve ultraviolet protection performance improvement effects even in combination with other common powder components (Examples 11-19).

On the other hand, when the specific hydrophobic powders that can be used in the present invention were not included, ultraviolet protection performance improvement effects were not able to be obtained even when equivalent amounts of other common powder components were blended (Comparative Examples 4 to 7).

Examples 20 and 21, and Comparative Example 8

The water-in-oil emulsion cosmetics having the compositions listed in Table 4 below were prepared, and the Abs variation rates before and after water immersion were determined in the same manner as that described above.

TABLE 4

|  | Ex. 20 | Ex. 21 | Comp. Ex. 8 |
|---|---|---|---|
| Octocrylene | 5 | 5 | 5 |
| 2-Ethylhexyl para-methoxycinnamate | 5 | 5 | 5 |
| 2,4-bis-[{4-(2-ethylhexyloxy)-2-hydroxy}-phenyl]-6-(4-methoxyphenyl)-1,3,5-triazine | 1.5 | 1.5 | 1.5 |
| Diethylamino hydroxybenzoyl hexyl benzoate | 1.5 | 1.5 | 1.5 |
| 4-tert-Butyl-4'-methoxydibenzoylmethane | 2 | 2 | 2 |
| Dextrin palmitate | 2 | 1 | — |
| Sucrose acetate stearate | 1 | 1 | — |
| Hydrogenated palm oil | — | 1 | — |
| Palm oil | — | 0.4 | — |
| Palm kernel oil | — | 0.6 | — |
| Trimethylsiloxysilicic acid | 1.5 | 1.5 | 1.5 |
| Polyoxybutylene (9) polyoxypropylene (1) glycol | 2 | 2 | 2 |
| Isostearic acid | 0.5 | 0.5 | 0.5 |
| Diisopropyl sebacate | 10 | 10 | 10 |
| Isopropyl myristate | 5 | 5 | 5 |
| Glyceryl tri-2-ethylhexanoate | 5 | 5 | 5 |
| Methyl polysiloxane | 3 | 3 | 3 |
| Dimethyl distearyl ammonium hectorite | 0.5 | 0.5 | 0.5 |
| Decamethylcyclopentasiloxane | 12 | 12 | 12 |
| Lauryl PEG-9 polydimethylsiloxyethyl dimethicone | 2 | 2 | 2 |
| Purified water | bal | bal | bal |
| Table salt | s.a. | s.a. | s.a. |
| Trisodium edetate | s.a. | s.a. | s.a. |
| Fragrance | s.a. | s.a. | s.a. |
| Glycerin | 2 | 2 | 2 |
| Alcohol | 10 | 10 | 10 |
| Hydrogendimethicone-treated pearling agent (mica/titanium oxide) | 2 | 2 | 2 |
| Crosslinked poly(methyl methacrylate) (average particle size 8 μm) low crosslink density type (crosslink density 10%) | 5 | 5 | — |
| Calcium stearate-treated talc (average particle size 7 μm) | 10 | 10 | — |
| Crosslinked silicone-network silicone block copolymer (average particle size 5 μm) | 0.5 | 0.5 | — |
| Abs variation rate (%) | 105.4 | 106.1 | 95.0 |

As shown in Table 4, it was confirmed that ultraviolet protection performance improvement effects were obtained even when changing the combination or the blended amount of the oil phase thickener (Examples 20 and 21).

On the other hand, when the specific hydrophobic powders that can be used in the present invention were not included, ultraviolet protection performance improvement effects were not able to be obtained after agitation while immersed in water (Comparative Example 8).

Examples 22 to 27, and Comparative Examples 9 and 10

The water-in-oil emulsion cosmetics having the compositions listed in Tables 5A and 5B below were prepared, and the Abs variation rates before and after water immersion were determined in the same manner as that described above.

TABLE 5A

|  | Comp. Ex. 9 | Ex. 22 | Ex. 23 | Ex. 24 |
|---|---|---|---|---|
| Purified water | bal | bal | bal | bal |
| Octocrylene | 5 | 5 | 5 | 5 |
| Diethylamino hydroxybenzoyl hexyl benzoate | 2 | 2 | 2 | 2 |
| 2,4-bis-[{4-(2-ethylhexyloxy)-2-hydroxy)-phenyl]-6-(4-methoxyphenyl)-1,3,5-triazine | 1 | 1 | 1 | 1 |
| Dextrin palmitate | — | 3 | 5 | 8 |
| Cetyl 2-ethylhexanoate | 5 | 5 | 5 | 5 |
| Glyceryl tri-2-ethylhexanoate | 5 | 5 | 5 | 5 |
| Diisopropyl sebacate | 5 | 5 | 5 | 5 |
| Dimethyl polysiloxane (*1) | 2 | 2 | 2 | 2 |
| Decamethylcyclopentasiloxane | 30 | 30 | 30 | 30 |
| Lauryl PEG-9 polydimethylsiloxyethyl dimethicone | 2 | 2 | 2 | 2 |
| Isododecane | 10 | 10 | 10 | 10 |
| Ethanol (*2) | 10 | 10 | 10 | 10 |
| Glycerin | 1 | 1 | 1 | 1 |
| Trisodium edetate | s.a. | s.a. | s.a. | s.a. |
| Fragrance | s.a. | s.a. | s.a. | s.a. |
| Table salt | s.a. | s.a. | s.a. | s.a. |
| Calcium stearate-treated talc (average particle size 7 μm) | 5 | 5 | 5 | 5 |
| Abs variation rate (%) | 66.9 | 154.5 | 148.0 | 138.6 |

(*1) KF-96A-6T (Shin-etsu Chemical Co., Ltd.)
(*2) Synthetic alcohol 95% (Japan Alcohol Trading Co., Ltd.)

TABLE 5B

|  | Comp. Ex. 10 | Ex. 25 | Ex. 26 | Ex. 27 |
|---|---|---|---|---|
| Octocrylene | 5 | 5 | 5 | 5 |
| 2-Ethylhexyl para-methoxycinnamate | 3 | 3 | 3 | 3 |
| 4-tert-Butyl-4'-methoxydibenzoylmethane | 2.5 | 2.5 | 2.5 | 2.5 |
| 2,4-bis-[{4-(2-ethylhexyloxy)-2-hydroxy)-phenyl]-6-(4-methoxyphenyl)-1,3,5-triazine | 2 | 2 | 2 | 2 |
| Diethylamino hydroxybenzoyl hexyl benzoate | 2 | 2 | 2 | 2 |
| Polyoxybutylene (9) polyoxypropylene (1) glycol | 2 | 2 | 2 | 2 |
| Isostearic acid | 0.5 | 0.5 | 0.5 | 0.5 |
| Diisopropyl sebacate | 10 | 10 | 10 | 10 |
| Isopropyl myristate | 5 | 5 | 5 | 5 |
| Glyceryl tri-2-ethylhexanoate | 5 | 5 | 5 | 5 |
| Polyamide-8 (*2) | — | 1 | — | — |
| N-Lauroyl-L-glutamic acid dibutyl amide (*3) | — | — | 1 | — |
| Glyceryl (behenate/eicosanedioate) (*4) | — | — | — | 0.5 |
| Trimethylsiloxysilicic acid | 1.5 | 1.5 | 1.5 | 1.5 |
| Methyl polysiloxane | 5 | 5 | 5 | 5 |
| Lauryl PEG-9 polydimethylsiloxyethyl dimethicone | 3 | 3 | 3 | 3 |
| Dimethyl distearyl ammonium hectorite | 0.5 | 0.5 | 0.5 | 0.5 |
| Decamethylcyclopentasiloxane | 12 | 12 | 12 | 12 |
| Calcium stearate-treated talc (average particle size 7 μm) | 5 | 5 | 5 | 5 |
| Crosslinked poly(methyl methacrylate) (average particle size 8 μm), low crosslink density type (crosslink density 10%) | 10 | 10 | 10 | 10 |
| Crosslinked silicone-network silicone block copolymer (average particle size 5 μm) | 1 | 1 | 1 | 1 |
| Purified water | bal | bal | bal | bal |
| Table salt | s.a. | s.a. | s.a. | s.a. |
| Trisodium edetate | s.a. | s.a. | s.a. | s.a. |
| Xylitol | 1 | 1 | 1 | 1 |
| Glycerin | 1 | 1 | 1 | 1 |
| Alcohol (*1) | 6 | 6 | 6 | 6 |
| Abs variation rate (%) | 95.6 | 106.9 | 107.3 | 105.4 |

(*1) Synthetic alcohol 95% (Japan Alcohol Trading Co., Ltd.)
(*2) Oleocraft LP-20 (Croda Japan K. K.)
(*3) GP-1 (Ajinomoto Healthy Supply Co., Inc.)
(*4) Nomucoat HK-G (The Nisshin Oillio Group, Ltd.)

As shown in Table 5A and Table 5B, strong ultraviolet protection performance improvement effects were obtained even when there was only one type of oil phase thickener (Examples 22 to 27). On the other hand, when an oil phase thickener was not included at all, the ultraviolet protection effect after agitation while immersed in water was markedly reduced, and ultraviolet protection performance improvement effects were not obtained (Comparative Examples 9 and 10).

As a result, it was confirmed that sufficient ultraviolet protection performance improvement effects can be obtained by blending a combination of at least one oil phase thickener and a hydrophobic powder.

Hereinafter, formulation examples of the water-in-oil emulsion cosmetic of the present invention will be described. Needless to say, the present invention is not in any way limited by these formulation examples and is rather defined by the claims. The blended amounts are all indicated in % by mass relative to the overall amount of the water-in-oil emulsion cosmetic.

Formulation Example 1. Base cosmetic

| (Component Name) | Blended amount (% by mass) |
| --- | --- |
| Octocrylene | 3 |
| Octyl salicylate | 3 |
| 2,4-bis-[{4-(2-ethylhexyloxy)-2-hydroxy}-phenyl]-6-(4-methoxyphenyl)-1,3,5-triazine | 1 |
| Diethylamino hydroxybenzoyl hexyl benzoate | 1 |
| Zinc oxide | 3 |
| Titanium oxide | 2 |
| Dextrin palmitate | 4 |
| Vaseline | 2 |
| Trimethylsiloxysilicic acid | 2 |
| Polyoxybutylene (9) polyoxypropylene (1) glycol | 2 |
| Isostearic acid | 1 |
| Diisopropyl sebacate | 8 |
| Mineral oil | 3 |
| Glyceryl tri-2-ethylhexanoate | 2 |
| Methyl polysiloxane | 3 |
| Decamethylcyclopolysiloxane | 20 |
| Polyoxyethylene-methyl polysiloxane copolymer | 2 |
| Purified water | balance |
| Table salt | s.a. |
| Trisodium edetate | s.a. |
| Fragrance | s.a. |
| Glycerin | 1 |
| Butylene glycol | 3 |
| Alcohol | 6 |
| Hydrogendimethicone-treated pearling agent (mica/titanium oxide) | 2 |
| Methylhydrogenpolysiloxane-treated pearling agent (mica/titanium oxide/iron oxide) | 1 |
| Calcium stearate-treated talc (average particle size 7 μm) | 5 |
| Silicic anhydride (average particle size 5 μm) | 1 |
| Crosslinked silicone-network silicone block copolymer (average particle size 5 μm) | 3 |
| Black iron oxide | 1 |
| Yellow iron oxide | 0.3 |
| Red iron oxide | 0.3 |

Formulation Example 2. BB Cream

| (Component Name) | Blended amount (% by mass) |
| --- | --- |
| Octocrylene | 5 |
| Homosalate | 10 |
| 4-tert-Butyl-4'-methoxydibenzoylmethane | 1 |
| Diethylamino hydroxybenzoyl hexyl benzoate | 2 |
| Titanium oxide | 5 |
| Sucrose acetate stearate | 3 |
| Microcrystalline wax | 1 |
| Trimethylsiloxysilicic acid | 3 |
| Polyoxybutylene (9) polyoxypropylene (1) glycol | 2 |
| Isostearic acid | 1 |
| Pentaerythritol tetra-2-ethylhexanoate | 8 |
| α-Olefin oligomer | 3 |
| Glyceryl tri-2-ethylhexanoate | 2 |
| Methyl polysiloxane | 3 |
| Dimethyl distearyl ammonium hectorite | 2 |
| Isododecane | 10 |
| Decamethylcyclopentasiloxane | 3 |
| Polyoxyethylene-methyl polysiloxane copolymer | 3 |
| Purified water | balance |
| Table salt | s.a. |
| Trisodium edetate | s.a. |
| Fragrance | s.a. |
| Sorbitol | 1 |
| Dipropylene glycol | 5 |
| Alcohol | 10 |
| Methyl polysiloxane-treated pearling agent (titanated mica) | 2 |
| Calcium stearate-treated talc (average particle size 7 μm) | 10 |
| Crosslinked silicone-network silicone block copolymer (average particle size 5 μm) | 8 |
| Black iron oxide | 1 |
| Yellow iron oxide | 0.7 |
| Red iron oxide | 0.3 |

Formulation Example 3. Whitening Milky Lotion

| (Component Name) | Blended amount (% by mass) |
| --- | --- |
| Octocrylene | 5 |
| Homosalate | 10 |
| 2-Ethylhexyl paramethoxycinnamate | 5 |
| Diethylamino hydroxybenzoyl hexyl benzoate | 3 |
| Titanium oxide | 1 |
| Zinc oxide | 3 |
| Sucrose acetate stearate | 3 |
| Dextrin palmitate | 2 |
| Trimethylsiloxysilicic acid | 3 |
| Polyoxybutylene (9) polyoxypropylene (1) glycol | 3 |
| Pentaerythritol tetra-2-ethylhexanoate | 5 |
| Diisopropyl sebacate | 12 |
| Glyceryl tri-2-ethylhexanoate | 5 |
| Methyl polysiloxane | 3 |
| Dimethyl distearyl ammonium hectorite | 1 |
| Isododecane | 10 |
| Decamethylcyclopentasiloxane | 5 |
| bis-Butyldimethicone polyglyceryl-3 | 1 |
| Purified water | balance |
| Tranexamic acid | 2 |
| 4-Methoxysalicylic acid potassium salt | 1 |
| Table salt | s.a. |
| Trisodium edetate | s.a. |
| Fragrance | s.a. |
| Glycerin | 3 |
| Dipropylene glycol | 3 |
| Alcohol | 8 |
| Calcium stearate-treated talc (average particle size 7 μm) | 5 |

Formulation Example 4. W/O-Type BB Cream

| (Component Name) | Blended amount (% by mass) |
| --- | --- |
| Purified water | balance |
| Alcohol | 5 |

| (Component Name) | Blended amount (% by mass) |
|---|---|
| Trisodium edetate | 0.1 |
| Table salt | 0.1 |
| Sodium pyrosulfite | 0.01 |
| Phenoxyethanol | 1 |
| Glycerin | 5 |
| Erythritol | 1 |
| Xylitol | 1 |
| Tormentilla extract | 0.1 |
| Sodium hyaluronate | 0.1 |
| 2-O-ethyl L-ascorbic acid | 0.1 |
| Dipotassium glycyrrhizinate | 0.05 |
| Isopropyl myristate | 5 |
| Glyceryl tri-2-ethylhexanoate | 5 |
| Diisopropyl sebacate | 5 |
| Alkyl ($C_{12-15}$) benzoate | 3 |
| Methyl polysiloxane | 6 |
| Cyclopentasiloxane | 6 |
| 50% Trisiloxysilicic acid in cyclopentasiloxane solution | 2 |
| Dextrin palmitate | 2 |
| 2-Ethylhexyl methoxycinnamate | 5 |
| Homosalate | 5 |
| Hydrophobically treated fine-particle titanium oxide (particle size 15 nm) | 3 |
| Hydrophobically treated fine-particle zinc oxide (particle size 15 nm) | 3 |
| Hydrophobically treated pigment-grade titanium oxide | 3 |
| Hydrophobically treated red iron oxide | s.a. |
| Hydrophobically treated yellow iron oxide | s.a. |
| Hydrophobically treated black iron oxide | s.a. |
| Hydrophobically treated talc | 3 |
| Crosslinked silicone-network silicone block copolymer (average particle size 5 μm) | 6 |
| Fine-particle dimethylsilylated silica | 0.5 |
| Lauryl PEG-9 polydimethylpolysiloxyethyl dimethicone | 2 |
| Dimethyl distearyl ammonium hectorite | 1 |
| Dextrin palmitate | 0.5 |
| Isostearic acid | 0.2 |
| Tocopherol | 0.01 |
| Fragrance | s.a. |

Formulation Example 5. W/O-Type Base Cosmetic

| (Component Name) | Blended amount (% by mass) |
|---|---|
| Purified water | balance |
| Alcohol | 10 |
| Trisodium edetate | 0.1 |
| Table salt | 0.1 |
| Sodium pyrosulfite | 0.01 |
| Glycerin | 1 |
| Xylitol | 1 |
| Tormentilla extract | 0.1 |
| Sodium hyaluronate | 0.1 |
| 2-O-ethyl L-ascorbic acid | 0.1 |
| Dipotassium glycyrrhizinate | 0.05 |
| Isododecane | 5 |
| Diisopropyl sebacate | 8 |
| Glyceryl tri-2-ethylhexanoate | 5 |
| Isopropyl myristate | 5 |
| PBG/PPG-9/1 copolymer | 2 |
| Methyl polysiloxane | 5 |
| Cyclopentasiloxane | 3 |
| Caprylyl methicone | 3 |
| 20% Highly polymerized aminopropyl dimethicone in dimethicone 20 cs solution | 1 |
| 50% Trifluoroalkyl dimethyl trimethylsiloxysilicic acid dimethicone solution | 3 |
| Dextrin palmitate | 2 |
| 2-Ethylhexyl methoxycinnamate | 5 |
| Diethylamino hydroxybenzoyl hexyl benzoate | 1 |
| bis-Ethylhexyloxyphenol methoxyphenyl triazine | 0.5 |
| Hydrophobically treated fine-particle titanium oxide (particle size 15 nm) | 2 |
| Hydrophobically treated fine-particle zinc oxide (particle size 15 nm) | 5 |
| Hydrophobically treated pigment-grade titanium oxide | 5 |
| Hydrophobically treated red iron oxide | s.a. |
| Hydrophobically treated yellow iron oxide | s.a. |
| Hydrophobically treated black iron oxide | s.a. |
| Hydrophobically treated talc | 5 |
| Crosslinked silicone-network silicone block copolymer (average particle size 5 μm) | 2 |
| Hydrophobically treated talc | 3 |
| PEG-9 polydimethylsiloxyethyl dimethicone | 1.5 |
| 50% PEG/PPG-19/19 dimethicone in cyclopentasiloxane solution | 0.5 |
| Dimethyl distearyl ammonium hectorite | 0.4 |
| Isostearic acid | 0.3 |
| Tocopherol | 0.01 |
| Fragrance | s.a. |

Formulation Example 6. W/O-Type Hair Cosmetic

| (Component Name) | Blended amount (% by mass) |
|---|---|
| Purified water | balance |
| Alcohol | 8 |
| Trisodium edetate | 0.2 |
| Silica | 0.5 |
| Glycerin | 1 |
| Polyoxyethylene (14) polyoxypropylene (7) dimethyl ether | 1 |
| *Rosa canina* fruit oil | 0.1 |
| Sodium hyaluronate | 0.1 |
| 2-O-ethyl L-ascorbic acid | 0.5 |
| Dipotassium glycyrrhizinate | 0.05 |
| Isododecane | 10 |
| Glyceryl tri-2-ethylhexanoate | 5 |
| Isopropyl myristate | 5 |
| Diisopropyl sebacate | 5 |
| Alkyl ($C_{12-15}$) benzoate | 3 |
| PBG/PPG-9/1 copolymer | 1 |
| Methyl polysiloxane | 10 |
| Cyclopentasiloxane | 3 |
| 50% Trisiloxysilicic acid in cyclopentasiloxane solution | 0.5 |
| Sucrose tetrastearate triacetate | 1 |
| Dextrin palmitate | 2 |
| 2-Ethylhexyl methoxycinnamate | 5 |
| Diethylamino hydroxybenzoyl hexyl benzoate | 2 |
| bis-Ethylhexyloxyphenol methoxyphenyl triazine | 1 |
| Polysilicone-15 | 3 |
| Octocrylene | 5 |
| Crosslinked silicone-network silicone block copolymer (average particle size 5 μm) | 10 |
| Calcium stearate-treated talc (average particle size 7 μm) | 3 |
| Cetyl PEG/PPG-10/1 dimethicone | 1 |
| Lauryl PEG-9 polydimethylpolysiloxyethyl dimethicone | 1 |
| Dimethyl distearyl ammonium hectorite | 0.5 |
| Isostearic acid | 0.3 |
| Sorbitan sesquiisostearate | 0.3 |
| Tocopherol | 0.01 |
| Fragrance | s.a. |

The invention claimed is:

1. A water-in-oil emulsion cosmetic, comprising:
   (A) 6 to 40% by mass of the cosmetic of an ultraviolet absorbing agent selected from the group consisting of 2-ethylhexyl para-methoxycinnamate, 2,4-bis-[{4-(2-ethylhexyloxy)-2-hydroxy}-phenyl]-6-(4-methoxy-phenyl)-1,3,5-triazine, diethylamino hydroxybenzoyl hexyl benzoate, octocrylene, 4-tert-butyl-4'-methoxydibenzoylmethane, octyl salicylate, homosalate, and polysilicone-15;
   (B) a dextrin fatty acid ester selected from the group consisting of dextrin palmitate, dextrin oleate, dextrin stearate, dextrin myristate, and dextrin palmitate/2-ethylhexanoate;
   (C) a fatty acid soap-treated talc; and
   (D) 0 to 6% by mass of an ultraviolet scattering agent relative to the mass of the cosmetic.

2. The water-in-oil emulsion cosmetic, according to claim 1, wherein the dextrin fatty acid ester is dextrin palmitate.

3. The water-in-oil emulsion cosmetic according to claim 1, wherein the fatty acid soap-treated talc is calcium stearate treated talc.

4. The water-in-oil emulsion cosmetic according to claim 2, wherein the fatty acid soap-treated talc is calcium stearate treated talc.

* * * * *